United States Patent [19]

Ghielmetti et al.

[11] Patent Number: 4,572,806

[45] Date of Patent: Feb. 25, 1986

[54] PROCESS FOR THE CONTINUOUS PRODUCTION OF TETRACHLOROPHTHALO-NITRILE IN TWO REACTORS IN SERIES

[75] Inventors: Giuseppe Ghielmetti, Milan; Liborio Casale; Giordano Donelli, both of Brescia, all of Italy

[73] Assignee: Caffaro S.p.A., Milan, Italy

[21] Appl. No.: 629,948

[22] Filed: Jul. 10, 1984

[30] Foreign Application Priority Data

Jul. 19, 1983 [IT] Italy ................................ 22129 A/83

[51] Int. Cl.$^4$ ............................................ C07C 121/56
[52] U.S. Cl. ................................................. 260/465 G
[58] Field of Search ..................................... 260/465 G

[56] References Cited

U.S. PATENT DOCUMENTS 3,839,401 10/1974 Lavergne et al. .............. 260/465 G
4,485,050 11/1984 Casale et al. ................... 260/465 G

*Primary Examiner*—Dolph H. Torrence
*Attorney, Agent, or Firm*—Young & Thompson

[57] ABSTRACT

In an improved process for the continuous production of tetrachlorophthalonitrile, of the type with activated carbon fluidized bed reactor, under whose grid melted and atomized phthalonitrile, chlorine, hydrochloric acid and possibly nitrogen are simultaneously introduced the use of a second static bed reactor, also of activated carbon, in series with the first, is provided for, thereby greatly improving the life of the catalyzer, and, above all, the quality of the product.

7 Claims, 1 Drawing Figure

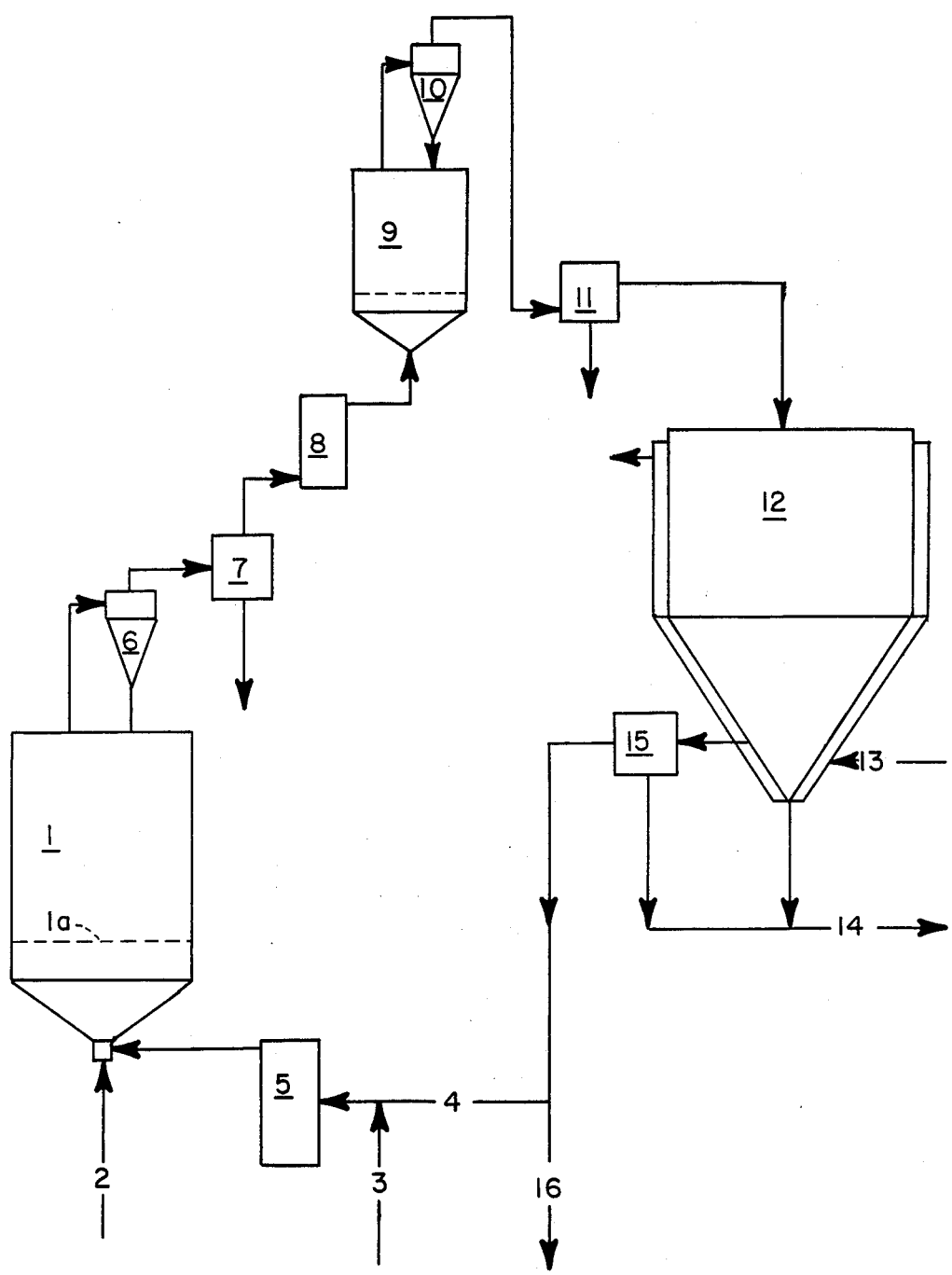

PROCESS FOR THE CONTINUOUS PRODUCTION OF TETRACHLOROPHTHALO-NITRILE IN TWO REACTORS IN SERIES

BACKGROUND OF THE INVENTION

Processes are already known for the production of tetrachlorophthalonitriles, and in particular of tetrachloroisophthalonitrile. In particular, we refer to U.S. Pat. No. 3,839,401 and U.S. Pat. No. 4,485,050.

These processes, like the majority of processes based on catalytic reactions in a fluidized bed, require carrying out an optimal fluidization, especially when wishing to obtain directly products with a high degree of purity.

On the other hand, the conditions required to optimize bed fluidization do not leave much margin for the operative conditions required to run the plant.

In practice, any occasional deviations from the prefixed temperature and flow intervals lead to the formation of hypo-chlorinated and super-chlorinated impurities and, in some cases, to a rapid decay in the catalytic activity of the bed.

This may involve both a variability in product purity and higher expenses due to the costs for replacing the catalyzer and to productivity losses caused by plant stoppage.

SUMMARY OF THE INVENTION

It has now been found that, if a second static bed reactor is inserted in series with a fluidized bed reactor of the type described in U.S. Pat. No. 4,485,050, so that, even under non-optimal conditions of fluidization, in the first reactor most of the chlorination and heat removal takes place while in the second, the reaction is completed, it is possible to work at a lower temperature, with a considerable increase in the life of the catalyzer, with a purity of the tetrachlorophthalonitrile produced always exceeding 98.5%, the hypo- or super-chlorinated impurities being minimized. Furthermore, the flow of reaction gases may exceed the limits for optimal fluidization of the first reactor (with a consequent increase in plant productivity), while maintaining the abovementioned high degree of product purity.

If we proceed in this way, in the second reactor of the plant which is operated according to the invention, it is possible to work with a static bed, as the problem of eliminating the reaction heat to prevent excessive and dangerous temperature rises does not exist, in that most of this heat is already eliminated in the first stage.

Substantially, the process according to the present invention is carried out similarly to that described and claimed in U.S. Pat. No. 4,485,050, but with the difference that the gas coming from the fluidized bed of the first reactor, where reaction may even be incomplete, after going through a system of carbon dedusting goes through a heat exchanger, then gets suitably cooled or heated, and is finally let into a second static catalytic bed, where the reaction is completed.

BRIEF DESCRIPTION OF THE DRAWINGS

The process is outlined in the single FIGURE of the accompanying drawing which shows how the bottom of a fluidized bed reactor 1 is simultaneously fed with melted isophthalonitrile flowing from 2, and with chlorine flowing from 3 together with recycled gas flowing from 4, through a heater 5.

DESCRIPTION OF THE PREFERRED EMBODIMENT

In the reactor 1 reaction takes place as indicated in U.S. Pat. No. 4,485,050.

The reaction gases and products, flowing from the top of the reactor 1, are sent to a centrifugal dust separator 6 and to a filter 7 arranged in cascade, to separate the carbon dust conveyed; then, after having been—if necessary—appropriately cooled or heated in an exchanger 8, they flow into a second static bed reactor 9.

After going through a possible centrifugal dust separator 10 and a filter 11, the gases and vapors from the second reactor 9 flow into the sublimator 12, cooled by 13. The solid product obtained is recovered at the bottom of the sublimator, through 14, while the exhaust gases are extracted, filtered in 15, and then partly removed through 16 and partly recycled through 4, as already seen.

The following conditions must be observed to obtain correct operation of the process:

the phthalonitrile at the inlet of the reactor 1 must be maintained at a slightly higher than melting temperature, in particular, for isophthalonitrile, preferably between 165° and 180° C.;

the gases must have a volume and temperature such as to evaporate the phthalonitrile without overheating it; their volumetric composition may vary between the following limits: $Cl_2$ between 30% and 50%, HCl between 30% and 70%, $N_2$ between 0 and 30%.

To obtain a mixture of gas (chlorine, plus hydrochloric acid and possibly another inert gas) and of phthalonitrile vapor at 180° C., use can be made for example, of 1.5 to 5 Nmc or more of these gases, heated to between 250° and 350° C., to evaporate 1 kg. of phthalonitrile melted at 170° C.

The quantity of chlorine in the gases must be such as to establish, with the phthalonitrile, a molar ratio between 7 and 20 and preferably between 10 and 15.

The reaction temperature in the fluidized bed of the first reactor 1 must be between 280° and 400° C.

The dwell time in this first reactor 1 may vary between 3 and 10 seconds.

The reaction temperature in the second reactor 9 must be between 280° and 450° C., as a function of its geometry, of the dwell times, etc. The dwell time in this second reactor 9 may vary between 3 and 10 seconds.

The following example will further illustrate the process according to the invention, without limiting its scope. In particular, the reference to the "iso" isomer of the phthalonitrile is in no way limitative.

EXAMPLE

In a first activated carbon fluidized bed reactor 1, 1 Kmole/hour of isophthalonitrile with a degree of purity over 99%, melted at 170° C., is continuously fed under the grid 1a, and is then vaporized with 22 Kmoles/hour of a mixture of chlorine and hydrochloric acid at a temperature of 250° C., the chlorine/isophthalonitrile molar ratio being equal to 10.

Due to evaporation of the melt, the temperature of the resulting gaseous mixture immediately drops to 170° C. and all the isophthalonitrile passes to the vapor stage.

The gaseous mixture goes through the catalytic layer, fluidizing it. The reaction heat is partly removed from the fluidized bed to limit the temperature of the bed and that of the gas flowing out from the same bed at approximately 300° C. Under these conditions the product contained in the gases has a titer of tetrachloroisophthalonitrile between 92 and 98%

The heat removed is used to heat the inflowing gases.

The vapors and gases flowing from the first reactor are introduced after the filtration of the carbon dust, into a second active carbon static bed reactor 9, where chlorination is completed; the temperature of the inflowing gases is regulated by a heat exchanger 8, to maintain the temperature in the second reactor between 290° and 310° C.

The outflowing vapors and gases are caused to go through a 40° C. cold chamber 12, where the chlorination products condense, while the gases go through a bag filter 15.

The dust collected in the filter is continuously conveyed via 14, together with that extracted in the condenser 12. Most of the gases (16.6 Kmoles/hour) are recycled in their present state, while the remaining 5.4 Kmoles/hour are treated to recover the reaction hydrochloric acid and the chlorine.

The product obtained, 0.98 Kmoles/hour, has a tetrachloroisophthalonitrile titer exceeding 98.5%.

We claim:

1. Process for the production of tetrachlorophthalonitrile, comprising simultaneously introducing into an activated carbon fluidized bed reactor melted and atomized phthalonitrile, chlorine, hydrochloric acid and possibly nitrogen in sufficient quantity to vaporize the phthalonitrile and maintain the bed of activated carbon fluidized, and passing gas from said reactor through an activated carbon static bed reactor.

2. Process as in claim 1, in which most of the chlorination (80-98%) is carried out in the first of said reactors, while reaction is completed in the second.

3. Process as in claim 1, in which in the first reactor, the temperature of the fluidized bed is between 280° and 400° C. and the contact time between 3 and 10 seconds, while, in the second reactor, the temperature of the static bed is between 280° and 400° C. and contact time is between 3 and 10 seconds.

4. Process as in claim 1, in which the melted isophthalonitrile is introduced into the first reactor at a temperature of between 165° and 180° C. from the bottom of the first fluidized bed reactor.

5. Process as in claim 1, in which the chlorine/isophthalonitrile molar ratio is between 7 and 20.

6. Process as in claim 1, in which the tetrachloroisophthalonitrile, separated from the gaseous reaction mixture through desublimation by simple cooling, is continuously recovered in the form of powder.

7. Process as in claim 1, in which most of the gaseous mixture resulting from separation of the tetrachlorisophthalonitrile is recycled and integrated with fresh chlorine to feed the fluidized bed of the first reactor, while the remaining part is removed from the system.

* * * * *